United States Patent [19]

Brooks et al.

[11] 4,267,119
[45] May 12, 1981

[54] SULFONATING METHOD

[75] Inventors: Burton Brooks, Bellevue; Richard J. Brooks, Seattle, both of Wash.

[73] Assignee: The Chemithon Corporation, Seattle, Wash.

[21] Appl. No.: 106,247

[22] Filed: Dec. 21, 1979

Related U.S. Application Data

[60] Division of Ser. No. 850,350, Nov. 10, 1977, Pat. No. 4,185,030, which is a continuation of Ser. No. 690,652, May 27, 1976, abandoned, which is a continuation-in-part of Ser. No. 393,192, Aug. 30, 1973, abandoned.

[51] Int. Cl.³ .......................................... C07C 130/00
[52] U.S. Cl. ........................... 260/458 R; 260/459 R; 260/505 S; 260/513 T; 260/504 R
[58] Field of Search ........... 260/458 R, 459 R, 513 T, 260/504 R, 505 S

[56] References Cited

U.S. PATENT DOCUMENTS

| | | | |
|---|---|---|---|
| 2,865,958 | 12/1958 | Davies et al. | 260/513 T |
| 3,255,240 | 6/1966 | Walfram et al. | 260/503 |
| 3,427,342 | 2/1969 | Brooks et al. | 260/458 |
| 3,535,339 | 10/1970 | Beyer et al. | 260/327 H |
| 3,923,728 | 2/1975 | Falk et al. | 260/505 S |
| 4,102,911 | 7/1978 | Majima et al. | 260/458 R |
| 4,163,751 | 8/1979 | Von der Mey et al. | 260/458 R |

*Primary Examiner*—James H. Reamer
*Attorney, Agent, or Firm*—Merriam, Marshall & Bicknell

[57] ABSTRACT

An organic reactant is sulfonated by injecting it into a stream of gas comprising sulfur trioxide, at a venturi, and the resulting reaction mixture is quenched with a stream of cooled, recycled reaction product immediately downstream of the venturi in a conduit in which particles of reaction mixture are agglomerated into a film of the recycle stream and in which additional sulfonation reaction occurs.

1 Claim, 3 Drawing Figures

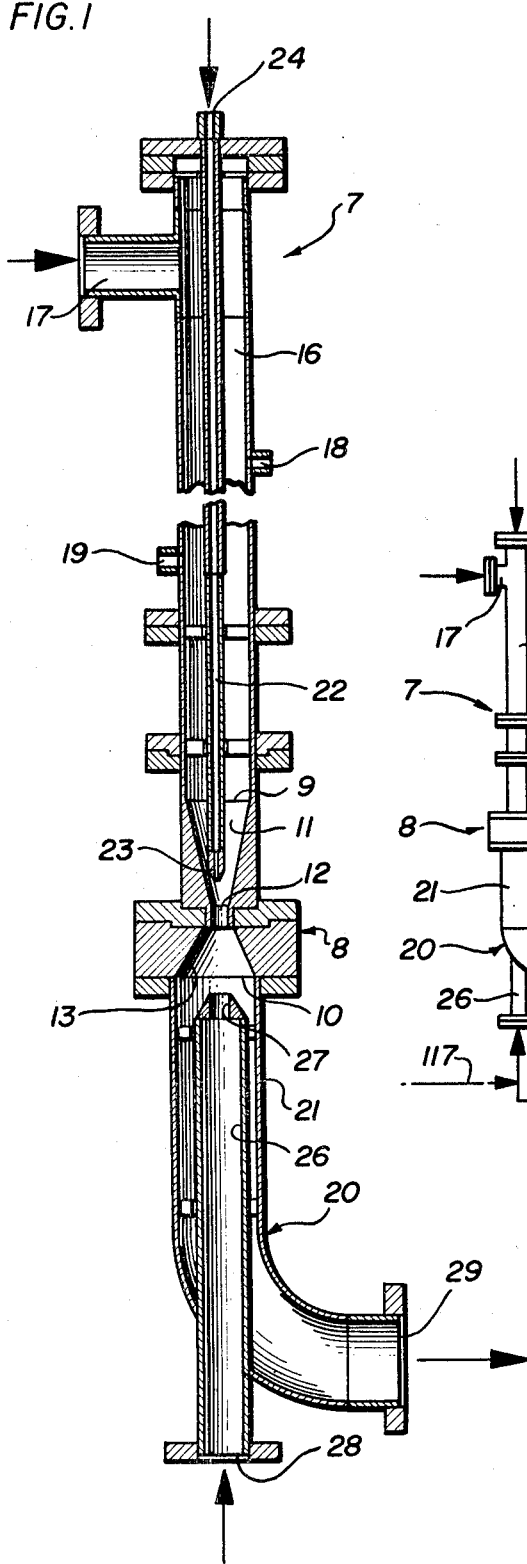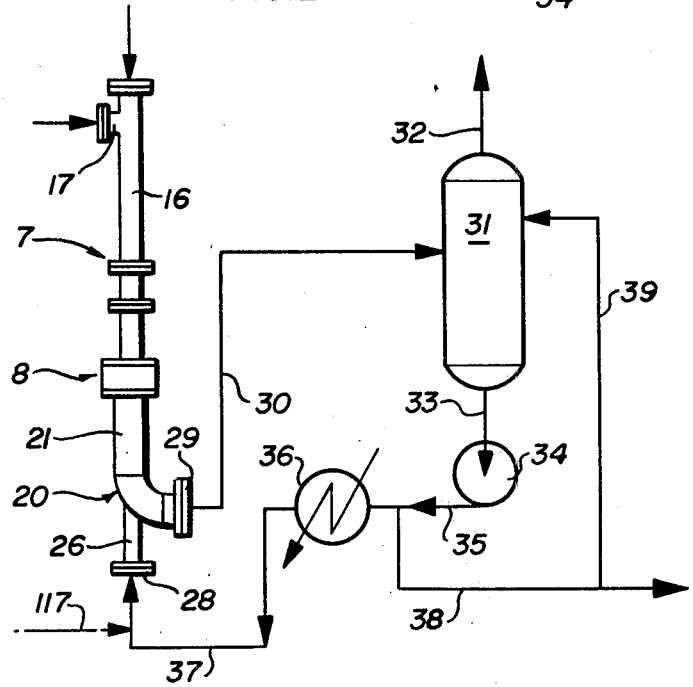

SULFONATING METHOD

This is a division of application Ser. No. 850,350, filed Nov. 10, 1977, now U.S. Pat. No. 4,185,030, which is a continuation of Ser. No. 690,652 filed May 27, 1976, which is a continuation-in-part of 393,192 filed Aug. 30, 1973 and now abandoned.

BACKGROUND OF THE INVENTION

The present invention relates generally to methods and apparatus for sulfonating an organic reactant with a gaseous sulfonating agent comprising sulfur trioxide ($SO_3$), and more particularly to such a sulfonating method and apparatus employing a venturi.

Many of the considerations involved, generally, in sulfonating a liquid organic reactant with a gaseous sulfonating agent comprising sulfur trioxide are discussed in Brooks et al. U.S. Pat. No. 3,427,342, issued Feb. 11, 1969, entitled "Continuous Sulfonation Process," especially Cols. 6-14, and the discussion therein is incorporated herein by reference.

As used herein, the term "organic reactant" refers to those materials, conventionally in liquid form, which heretofore have been subjected to a sulfonating reaction employing sulfur trioxide. A description of such materials is contained in said Brooks et al. U.S. Pat. No. 3,427,342, at Cols. 6-7, and said description is incorporated herein by reference.

The term "gaseous sulfonating agent comprising sulfur trioxide" refers to those gaseous agents which have heretofore been used to sulfonate organic reactants with sulfur trioxide, usually a dilute mixture of sulfur trioxide in an inert gas such as air. Examples of such gaseous agents and of procedures for preparing sulfur trioxide are described in said Brooks et al. U.S. Pat. No. 3,427,342 at Col. 7, and that description is incorporated herein by reference.

As used herein, the term "sulfonating" is used sometimes in its generic sense, applying to both true sulfonating and sulfating, and sometimes in its specific sense applying only to true sulfonating. The actual meaning intended will be apparent to those skilled in the art from the content in which the term is used.

Typically, a venturi comprises a tubular member having an approach zone with side walls converging in a downstream direction toward a throat or constriction which is the narrowest point of the venturi. Downstream of the throat is a recovery zone having side walls diverging from the throat. A fluid flowing through a venturi is accelerated and undergoes a pressure drop in the approach zone. In the venturi throat, the velocity is higher and the pressure lower than upstream thereof.

In a sulfonating reaction employing a venturi, the organic reactant and the gaseous sulfonating agent are reacted while flowing through the venturi, and the sulfonating reaction generates a large amount of heat in the venturi which can burn and discolor the reaction product, usually a sulfonic acid or alcohol sulfonate. A charred or discolored reaction product is usually undesirable, especially where the reaction product is to be used in the manufacture of detergents. It is also possible that particles of liquid reaction product may adhere to the walls of the venturi which also could cause undesired charring and discoloration of the particles of reaction product.

Other considerations arising when sulfonating in a venturi include obtaining a high yield (i.e., converting the highest possible percentage of organic reactant into reaction product) and processing large volumes of material without sacrificing quality or yield.

SUMMARY OF THE INVENTION

The present invention relates to a method and apparatus for conducting a sulfonating reaction in a venturi while (1) preventing the reaction product from being charred or discolored, (2) obtaining a high yield and (3) processing large volumes of material.

Essentially, liquid organic reactant is injected into a stream of gaseous sulfonating agent in the approach zone of the venturi, without prior contact between the reactants. The venturi may be cooled or uncooled. The gaseous sulfonating agent comprises 2-10 vol. % sulfur trioxide, and the balance is air. The ratio of sulfur trioxide to organic reactant is usually stoichiometric (i.e., the theoretical amount required to completely react all of the organic reactant), although there may be a slight stoichiometric excess or deficiency of sulfur trioxide depending upon the organic reactant. The stoichiomeric considerations involved are discussed in said Brooks et al. U.S. Pat. No. 3,427,342 at Cols. 7-8.

At the time the gaseous sulfonating agent contacts the organic reactant in the venturi, the gas has a velocity sufficiently high to atomize the liquid organic reactant into a mist of fine particles.

The sulfur trioxide gas is substantially (but not completely) absorbed by and reacted with the fine particles of organic reactant as the latter are conveyed through the venturi by the gas. The reaction mixture leaving the venturi comprises the reaction product (e.g., sulfonic acid), unreacted particles of liquid organic reactant, unreacted sulfur trioxide (to a large extent absorbed in the fine particles of liquid) and inert gas (air). The reaction mixture moves through the venturi, from the time of initial contact between the gaseous sulfonating agent and the liquid organic reactant until the time the reaction mixture passes out of the venturi, in less than one-tenth of a second.

The reaction mixture leaves the venturi at a temperature in the range 100°-350° F. Located immediately downstream of the venturi is a quenching zone. In the quenching zone, the reaction mixture, consisting essentially of particles of liquid in a gaseous carrying medium, are subjected to a quenching stream of cooled, recycled, liquid reaction product. In addition, the fine particles of liquid leaving the venturi are agglomerated into the quenching liquid by flowing the reaction mixture along a confined path parallel with and between adjacent films of cooled, liquid reaction product moving in a downstream direction. Unreacted sulfur trioxide entering the quenching zone with the reaction mixture undergoes substantial absorption by and reaction with unreacted organic reactant in the quenching zone, both with that unreacted organic reactant entering the quenching zone from the venturi zone and that entering the quenching zone with the recycle stream.

The length of time spent in the venturi, following the initial contact of the reactants, is very short (e.g., as low as 0.001-0.01 second or less), and the sulfonating reaction is generally only partially completed in the venturi. The remainder of the reaction between unreacted organic reactant and unreacted sulfur trioxide in the reaction mixture is essentially completed during cooling, agglomeration and recycling of the reaction product. Upon leaving the venturi, the reaction is usually about 20-97% complete and the major part of the remainder of the reaction occurs in the quenching zone. The factors which effect the extent of the reaction in the venturi and quenching zones will be subsequently discussed.

The temperature within the venturi may be relatively high, but the time the reaction product spends in the venturi, before quenching, is usually too short to allow charring to occur. The speed of the gas moving through the venturi is usually sufficiently high to strip from the walls of the venturi any particles of liquid which may have a tendency to adhere thereto, adherence to the hot walls of the venturi causing charring.

Moving the reaction mixture through the venturi at such high speeds while still effecting a substantial reaction therein allows high production rates.

The venturi-type reactor of the present invention has many advantages over film-type reactors such as that described in Brooks et al. U.S. Pat. No. 3,427,342 in that the venturi-type reactor is much simpler to build, operate and maintain, and the cost of construction and maintenance is less. With the venturi-type reactor, careful attention need not be paid to the distribution of the organic reactant as a film along the walls of the reactor, and there need not be periodic cleaning of accumulations of gunk or tarry material from the reactor walls which accumulations can cause heat transfer problems in film-type reactors. A relatively small venturi-type reactor is capable of large production capacities.

A process in accordance with the present invention can be operated at much higher sulfur trioxide concentrations (e.g., up to 7–10%) and correspondingly less diluent air than processes using film-type reactors while still producing equivalent product quality. This is because a substantial part of the reaction can be made to occur in the quenching section where burning of the reaction product is less likely than in a reaction zone upstream of the quenching zone.

Moreover, by operating with a smaller volume of diluent air, less power is required to operate the air blower and there is a reduction in the size of the gas-handling auxiliary equipment, such as air dryers, gas separators, effluent scrubbers, gas conduits, etc. Alternatively, the same size of equipment can be used to increase the production capacity of the plant compared to the same plant's capacity when using the lower concentration of sulfur trioxide and increased diluent air.

The decrease in diluent air for an increase in sulfure trioxide concentration from 4% to 8% is quite substantial. In the former case (4% concentration) there are 24 parts of air to one part of sulfur trioxide while in the latter case (8% concentration) there are only about 12 parts of air to one part of sulfur trioxide, a reduction in diluent air of one-half.

Other features and advantages are inherent in the struture claimed and disclosed or will become apparent to those skilled in the art from the following detailed description in conjunction with the accompanying diagrammatic drawing.

BRIEF DESCRIPTION OF THE DRAWING

FIG. 1 is a fragmentary sectional view of an apparatus for reacting a liquid organic reactant with a gaseous sulfonating agent in accordance with an embodiment of the present invention;

FIG. 2 is a flow sheet illustrating a method in accordance with an embodiment of the present invention; and FIG. 3 is a an enlarged fragmentary view of a portion of a device for injecting organic reactant in accordance with an embodiment of the present invention.

DETAILED DESCRIPTION

Referring initially to FIG. 1, indicated generally at 7 is a reactor constructed in accordance with an embodiment of the present invention. Reactor 7 includes a venturi indicated generally at 8 and comprising, in downstream sequence, an upstream end 9, an approach zone 11 having side walls converging in a downstream direction, a throat 12, a recovery zone 13 having side walls diverging in a downstream direction and a downstream end 10. A first conduit 16 communication with venturi approach zone 11 and is axially aligned therewith. Conduit 16 includes an inlet 17 extending to one side of conduit 16, and ports 18, 19 for inserting temperature and pressure measuring devices.

A second conduit indicated generally at 20 includes an upstream portion 21 communicating with downstream end 10 of venturi 8 and axially aligned with the venturi immediately downstream thereof.

Located concentrically within first conduit 16 is a third conduit 22 terminating at fluid injection means 23 located within venturi approach zone 11. Third conduit 22 includes an inlet 24 at the upstream end thereof.

Located concentrically within the upstream portion 21 of second conduit 20 is a fourth conduit 26 terminating at liquid outlet means 27 adjacent downstream end 10 of venturi 8. Outlet means 27 may extend into venturi recovery zone 13. Located at the opposite end of fourth conduit 26 is a liquid inlet 28.

Referring now to both FIGS. 1 and 2, second conduit 20 has an outlet 29 communicating with one end of a line 30 having another end leading into a liquid cyclone separator 31. Communicating with the top of cyclone separator 31 is a vent line 32, and communicating with the bottom of cyclone separator 31 is an outlet line 33 communicating with a pump 34 from which extends a line 35 leading to a heat exchanger 36 from which extends a line 37 leading to inlet 28 in fourth conduit 26.

Also extending from pump outlet line 35 is another line 38 from which extends a branch line 39 leading back to cyclone separator 31.

In an alternative embodiment, a branch line (not shown) may extend from recycle line 37 to a slit (not shown), extending around the periphery of venturi recovery zone 13 or just below venturi throat 12, for introducing cooled, recycled liquid into recovery zone 13 at the slit. Such a recycle slit is particularly desirable when sulfonating olefins.

First conduit 16, through which the gaseous sulfonating agent is introduced into the venturi, preferably has a straight length of approximately 10 pipe diameters upstream of venturi 8. This is desirable to smooth out the flow and distribution of the gas, following movement of the gas around a curve or elbow or corner such as at inlet 17.

Injection means 23, through which liquid organic reactant is injected into the gas stream at venturi approach zone 11, usually comprises a plurality of small holes around the periphery of a tube perfectly centered within venturi approach zone 11 (although only one hole is shown in FIG. 1). For example, given a conduit 22 of $\frac{3}{8}$" diameter, located inside a venturi approach zone 11 converging to a venturi throat 12 having a 1" diameter, the injection means 23 would have 8 holes, each having a diameter of 1/32', directed at a 45° down and out angle into venturi approach zone 11.

In a typical operation utilizing the reactor 7, gaseous sulfonating agent is introduced through inlet 17 into first conduit 16. Simultaneously, a liquid organic reactant is introduced through inlet 24 into third conduit 22. The gaseous sulfonating agent flows downstream through conduit 16 into venturi approach zone 11, and the liquid organic reactant is injected into the stream of gaseous sulfonating agent in venturi approach zone 11 through injecting means 23. There is no prior contact between the liquid organic reactant and the gaseous sulfonating agent upstream of venturi approach zone 11. The organic reactant is injected as a relatively fine stream (i.e., a stream with a small cross-sectional area) compared to the cross-sectional area of the gas stream into which it is injected.

Upon injection of the organic reactant into the gaseous sulfonating agent at approach zone 11, the organic reactant is atomized by the high speed gas into a fine mist which absorbs and reacts with the sulfur trioxide in the gaseous sulfonating agent. The reaction mixture thus formed continues to move through and out of the venturi 8 in a downstream direction.

To further assist in the atomization of the liquid organic reactant, an injector of the type illustrated in FIG. 3 may be utilized. In this embodiment organic reactant is introduced at 49 into an inner pipe 50 located concentrically within an outer pipe 51 into which air is introduced at 52. The organic reactant leaves pipe 50 at 53 to mix with the air downstream thereof in pipe 51 and at least partially atomize the organic reactant. The mixture of air and organic reactant is then injected into the stream of sulfur trioxide at the venturi approach zone through a lower opening 54 in pipe 51 which extends concentrically within conduit 16. The volume of air introduced at 52 is about 10% of the total volume of air which enters the venturi, the other 90% being introduced into conduit 16 with the sulfur trioxide at 17. Typically, pipe 50 has an inner diameter of ⅛ inch while pipe 51 has an inner diameter of about ½ inch and a lower opening 54 of about 1/5 inch.

Atomization may also be accomplished by injecting the liquid organic reactant as a film at the periphery of the venturi (e.g., through a peripheral slit in the approach zone) and providing a gas velocity sufficiently high (e.g., 350 feet per second or higher) to assure atomization.

After leaving venturi 8, the reaction mixture is flowed along a confined path, downstream of the venturi, defined by conduit 20. The reaction mixture is quenched, to cool the mixture, no later than immediately after the mixture leaves venturi 8. The reaction mixture, at the start of the quenching step, is in the form of fine particles of liquid in a gaseous carrying medium. Quenching is accomplished by contacting the reaction mixture with a moving volume or a mass of cooled, recycled liquid reaction product introduced into the reactor through fourth conduit 26 via outlet means 27 at the terminal end of conduit 26. A stream of cooled liquid reaction product initially contacts the reaction mixture at downstream end 10 of venturi 8 or slightly upstream thereof, and the quenching liquid is continually renewed at this location of initial contact between the reaction mixture and the quenching liquid. The quenching liquid then flows through conduit 20 along a path coinciding with the flow path of the reaction mixture coming from the venturi, with the quenching liquid assuming the form of a film along the outside walls of fourth conduit 26 and a film along the inside walls of second conduit 20.

Thus, the particles of reaction mixture are flowed in a downstream direction along a confined path having a predetermined cross-section, and part of the moving volume of quenching liquid is located at an interior portion of that cross-section.

By flowing the quenching liquid as a film along a path parallel to and adjacent that of the reaction mixture, there is provided repeated contact between the fine particles of reaction product and the film of cooled liquid reaction product thereby causing the fine particles to agglomerate. A factor in the continuous contacting of the fine particles of liquid reaction product with the film of cooled liquid reaction product is the presence, in conduit 20, of gas eddies which repeatedly impinge the fine particles against the recycled quenching liquid flowing down the walls of conduits 20 and 26.

The mixture of liquid and spent gas leaves second conduit 20 through outlet 29 and flows through line 30 into cyclone separator 31 where the gas is separated from the liquid, the gas being withdrawn through vent line 32 and the liquid (consisting essentially of reaction product) being removed through line 33.

Part of the liquid removed from the bottom of cyclone separator 31 through line 33 is pumped by pump 34 through line 35 to heat exchanger 36 from which cooled liquid reaction product is recycled through line 37 back to fourth conduit 26, as quenching liquid. Another part of the liquid removed from the bottom of cyclone separator 31 is pumped through a line 38 to additional processing stages which will vary with the material being processed but could include digestion, hydration, neutralization and hydrolysis. A portion of the liquid reaction product moving through line 38 is recycled through branch line 39 back to cyclone separator 31 to wash the walls of cyclone separator 31 and prevent the buildup thereon of over-reacted material.

As previously indicated, only part of the reaction usually occurs in venturi 8. Additional reaction takes place in conduit 20, the recycle loop (30, 31, 33–37) illustrated in FIG. 2 and downstream thereof.

As noted above, the principal reacting step, the quenching step and the agglomerating step occur in sequence, in respective zones, and, as shown in the drawing, there is no heat exchange surface in any of these zones. Thus, there is no external cooling of the film of quenching liquid to remove heat from the film while it undergoes repeated contact with the particles from the reaction mixture.

The variables in the venturi section that effect the final product quality (unreacted content and color) are: the gas velocity at the venturi throat, the gas velocity at the point of injection of the organic reactant, the temperature of the reaction mixture leaving the venturi, the residence time between (a) the organic reactant injection point and (b) the point in the quench section where quenching begins, and, to some extent, the dimensions of the venturi (length and throat diameter). These variables are all interrelated and are primarily responsible for the degree of completion of the reaction in the venturi. If the quenching section following the venturi section is designed as described herein to efficiently react unreacted organic reactant and sulfur trioxide leaving the venturi section, then it is not necessary to complete the absorption and reaction of sulfur trioxide by and with organic reactant in the venturi. If the reaction is not completed in the venturi, there is more leeway to provide optimum operating conditions. The above-noted variables will now be discussed in greater detail.

A fine mist of organic reactant is important to optimize contact, reaction and absorption of the sulfur trioxide with the organic reactant. The gas velocity is the venturi throat effects the degree of atomization of the organic reactant and this governs the degree of reaction completion. A high throat velocity produces a high degree of atomization and will drive the sulfonation reaction to completion, and this, in turn, increases the reaction mixture temperature at the venturi throat; but it also decreases the residence time before the reaction mixture is quenched.

When operating at a throat velocity of 700–900 feet per second, the sulfonation reaction will go to over 90% completion, resulting in a throat temperature of 200°–300° F. When operating at a throat velocity of 400–600 feet per second, the reaction is only 30%–60% completed in the venturi, and the throat temperature will range between 120°–200° F. If the cooling section following the venturi is designed for efficient reaction of the unreacted sulfur trioxide and organic reactant, as described herein, acceptable product can be produced with venturi throat velocities between 300–900 feet per second. Above 900 feet per second, the energy required due to pressure drop becomes quite large and impairs the practicality of the process.

The gas velocity at the liquid injection point also effects atomization of the liquid organic reactant and the degree of reaction completion. High velocities at the point of injection will give a high degree of reaction completion even with lower throat velocities. However, the final product quality is poorer, probably due to uneven atomization and over-reaction of some reaction mixture particles. The optimum range for this gas velocity is between 50–200 feet per second.

The approach zone 11 and the throat 12 of the venturi may be uncooled. However, the length of time spent by particles of liquid reaction product moving through the venturi is less than 0.1 second, so that the likelihood of the reaction product being charred or discolored, even within an uncooled venturi, is virtually non-existent. Any tendency of liquid particles to adhere to the walls of approach zone 11 or throat 12 of the venturi, an occurrence which could cause charring of the adhering particles, is prevented by the relatively high velocity of the gas moving through the venturi. To prevent adherence usually requires a gas velocity greater than 250 feet per second, the particular velocity depending upon the venturi temperature, the viscosity of the particles, etc.

At constant gas velocities, the length of the venturi directly governs the extent of reaction completion in the venturi. The length can be shortened, in effect, by introducing part of the cooled recycle stream into the venturi recovery section 13 just below throat 12, e.g., through a peripheral slot in section 13. If the reaction is only 30%–60% completed in the venturi, the length thereof is not so critical. In all cases, the reaction time before quenching is less than 0.1 second.

At a constant gas flow into the venturi, the venturi diameter determines the gas velocity at the venturi throat. The diameter also affects the reaction time by wall effect. In a small diameter unit there are more collisions by droplets of reaction product with the venturi wall, and this tends to increase the residence time in the venturi. Normally, as the venturi diameter is increased for longer capacity plants, the length-to-diameter ratio remains constant, and this results in approximately constant reaction time.

The sulfonation reaction with sulfur trioxide, being highly exothermic, results in an instantaneous increase in the temperature of the reaction product. The resulting temperature at the venturi throat will depend on the degree of completion of the reaction, the temperature of the feeds entering the reactor, and the percentage of inert diluent (air) introduced with the sulfur trioxide. With normal operation, this temperature is between 150°–200° F. If the liquid organic reactant is refrigerated and the inert diluent is high, the temperature could run below 100° F. At high sulfur trioxide concentrations, with the majority of the reaction occurring in the venturi, the temperature can range between 200°–300° F.

As previously noted, the quenching section, located immediately downstream of the venturi section, serves three functions: cooling the reaction mixture, agglomerating the fine particles of liquid, and reacting unreacted sulfur trioxide and liquid organic reactant. Each of these functions is discussed in more detail below.

With respect to cooling, the reaction mixture leaving the venturi could be at a temperature in the range 150°–350° F., and if it is allowed to remain at this temperature for even one second, the reaction product will darken considerably. For this reason, the temperature of the reaction mixture must be cooled immediately after leaving the venturi. This can be done by injecting the material leaving the venturi directly into a tank of cooled reaction product (e.g., sulfonic acid). However, utilizing a quenching procedure of the type illustrated in the figures is preferable. The recycled reaction product is cooled to a temperature above freezing and whose level depends upon the particular reaction product and the subsequent processing steps.

For example, when sulfonating linear alkyl benzene, the reaction product should be cooled below 130° F., and excellent product can be made by cooling the reaction product to within 90°–120° F.

Branched chain alkyl benzene sulfonates become quite viscous below 100° F., but very good quality can be obtained when the reaction product is cooled in the range 120°–140° F.

With lauryl alcohol and $C_{14}$–$C_{16}$ alpha-olefins, acceptable quality is produced when the reaction product is cooled to a temperature in the range 90°–100° F. However, excellent quality is produced when refrigerated water is used in heat exchanger 36 to cool the reaction product undergoing recycling and provide a quenching liquid having a temperature in the range 50°–60° F. for alpha-olefins and about 60° F. for lauryl alcohol.

The ratio of cooled, recycled reaction product to reactants is also important. This is because it is necessary to cool not only the reaction product but also the spent gas (mostly air). Therefore, a relatively large quantity of recycled quenching liquid is required. The weight ratio of recycled liquid to reactants should be at least 10–1, and as much as 60–1 is required to cool the reaction product below 100° F. from a temperature in the range 200°–350° F.

With respect to the agglomeration function of the quenching section, the reaction product leaving the venturi is very finely atomized. The majority of these particles are less than 0.050 inch diameter and some are less than 0.010 inch diameter. These particles are too small to be collected in a standard cyclone separator. Therefore it is necessary to agglomerate the particles in order to get a good yield of reaction product downstream of the reactor. As previously explained this is accomplished by repeated contact between the reaction mixture leaving the venturi and the recycled, cooled, liquid reaction product. Repeated contact can be accomplished using a second stage venturi similar to that illustrated in FIG. 1, only located downstream of the first venturi and with the reaction mixture being injected into a stream of quenching liquid.

However, repeated contact is best accomplished by utilizing the apparatus and procedure illustrated in FIG. 1 wherein the recycled cooling liquid flows as a film across a surface parallel with and adjacent to the flow of the reaction mixture leaving the venturi. Repeated contacting of the film of quenching liquid and the reaction mixture will result in agglomeration of the fine particles of liquid reaction product providing a separation of the liquid reaction product from the spent gas of over 99.8% with less than 0.2% of the liquid reaction product passing off with the gas through vent line 32 from cyclone spearator 31.

Typically, the length of the contacting zone in conduit 20 is at least 6" and preferably 12–48". Typically, the annular clearance between the two conduits 21 and 26 is about 0.7", and the liquid film on the walls of each of these two conduits is about 0.12–0.2" thick. In such a situation, the actual gas velocity moving through conduit 20 should be in the range of about 100–250 feet per second. For a conduit 20 and conduit 26 of given dimensions, the velocity of the gas flowing through the annulus between conduits 20 and 26 can be controlled by controlling the volume of the gas entering conduit 20 and the volume of the recycle liquid.

There is usually a pressure drop of 2–6 psig in quenching conduit 20 (3–4 psig preferred). A pressure drop in this range is needed in conduit 20 in order to provide a sufficient amount of contacting therein between the films of liquid quenching agent and the reaction mixture leaving venturi 8. Sufficient contacting is required in order to perform the three functions occurring in quenching conduit 20, namely cooling the reaction mixture, agglomerating the fine particles of liquid, and accomplishing at least part of the sulfonation reaction.

The sulfonation reaction in the quenching section occurs when unreacted sulfur trioxide entering conduit 20 is absorbed by and reacts with liquid organic reactant entering conduit 20 from the venturi section. In addition, unreacted sulfur trioxide is absorbed by the recycle stream entering conduit 20 from conduit 26 and reacts with unreacted organic reactant in the recycle stream. The last-described reaction is abetted by the relatively high gas velocity in the quenching section (100–250 feet per second) which controls the thickness of the recycle film in conduit 20 (0.12–0.20 inch thick) so that the sulfur trioxide can penetrate the film and react with unreacted organic reactant therein at all levels of the film.

The cooled recycle stream entering conduit 20 contains about 2–5 wt.% of, as yet, unreacted organic reactant, and the ratio of (a) recycle stream to (b) sulfur trioxide feed plus organic reactant feed is sufficiently high (e.g., 35 to 1) to maintain, in conduit 20, an excess of organic reactant to sulfur trioxide. This avoids undesirable over-reaction by the sulfur trioxide with the reaction product, which could occur in the absence of unreacted organic reactant.

The concentration of sulfur trioxide in the quenching section is much more dilute than in the venturi section because much of the sulfur trioxide has already been consumed in reaction in the venturi section. Therefore, in the quenching section, the reaction is milder and there is less chance of burning than with a high concentration of sulfur trioxide.

As noted above, about 20–97% of the sulfonation reaction occurs in the venturi section, with the major part of the remainder of the reaction occurring in the quenching section. For example, where 30% of the reaction occurs in the venturi section, up to 65% of the reaction can occur in the quenching section.

As an alternative to sulfonating in both the venturi and quenching sections, with many raw materials (e.g., alkyl benzenes) the sulfonation reaction may be initiated in the quenching section, dispensing entirely with the venturi section as a reaction zone or eliminating it entirely. In such an embodiment the sulfur trioxide would be injected directly into the upstream end of the quenching section to be absorbed by the films of recycle stream in conduits 20 and 26, and the liquid organic reactant would be introduced into the recycle stream before the recycle stream entered conduit 26 (e.g., through line 117 shown in phantom in FIG. 2). In such an embodiment, almost all of the sulfonation reaction occurs in the quenching section and the remainder occurs downstream of the quenching section.

Following is a summary of examples of operating conditions for both the venturi and quenching sections, which conditions will produce a good product for virtually all organic reactants to be sulfonated.

Venturi Section

Liquid organic reactant injection through multiple holes.

Actual gas velocity at liquid injection point—100 feet/second.

Actual gas velocity at venturi throat—400–550 feet/second.

Temperature at venturi throat—120°–160° F.

Pressure drop through venturi—4–7 psig.

Quenching Section

Actual gas velocity at upstream end—110 feet/second minimum.

Actual gas velocity at downstream end—130 feet/second minimum.

Liquid to gas ratio,
   by weight—30/1.
   by volume—1/25.

Recycle ratio [(a) recycled liquid to (b) organic reactant feed plus sulfur trioxide feed]—35/1.

Estimated film thickness—0.12–0.2".

Pressure drop—3–4 psig.

Calculated Reynolds No. of liquid film—100–200.

Following are examples of processes reflecting the sulfonating of organic reactants with sulfur trioxide in reactors employing venturis.

EXAMPLE I

Linear Dodecyl Benzene Sulfonate

Linear dodecyl benzene (the organic reactant) was sulfonated in a reactor, having a 1-inch venturi throat, under the following conditions:
Organic Reactant Flow Rate—600#/hr.
$SO_3$ Flow Rate—216#/hr.
$SO_3$ Concentration—6.5 vol. %
$SO_3$/Organic Reactant Mol Ratio—1.07/1
Air Flow Rate—250 SCFM
Venturi Diameter at Throat—1"
Reaction Path Length—8"
Gas Pressure at Upstream End of Venturi—10-13 PSIG
Pressure at Venturi Throat—6 PSIG
Approximate Gas Velocity at Venturi Throat—550 Ft./Sec.
Approximate Gas Velocity at Organic Reactant Injection Point—160 Ft./Sec.
Ratio of Recycle Quench to Reactants—40 to 1
Quenching Liquid Temperature—115° F.
Gas Velocity in Agglomeration Section—130 Ft./Sec.

The reaction product leaving the recycle loop was pumped through a digestion pipe for an additional 30 minutes hold-time; then 1% water was added to break any anhydride.

The resulting product (essentially alkyl benzene sulfonic acid) had an analysis reflecting the following:
Free Oil (Petroleum Ether Extract Procedure)—1.9 wt.%, active basis
Free Oil (Glycol Distillation Procedure)—0.7 wt.%, active basis
Sulfuric Acid—1.7 wt.%
Klett Color (5% solution 40 mm. path)—40

"Free Oil" is an indicator of unreacted organic reactant. A Klett Color number less than 50 indicates excellent color. A Klett Color number between 50 and 100 indicates acceptable color, in most cases.

EXAMPLE II

Alcohol Ether Sulfate

Ethoxylated fatty alcohol was sulfated in a reactor, having a 1-inch venturi throat, under the following conditions:
Organic Reactant Flow Rate—600#/hr.
$SO_3$ Flow Rate—165#/hr.
$SO_3$/Organic Reactant Mol Ratio—1.03/1
$SO_3$ Concentration—5 vol. %
Air Flow Rate—250 SCFM
Venturi Diameter at Throat—1"
Reaction Path Length—8"
Pressure at Upstream End of Venturi—10-13 PSIG
Pressure at Venturi Throat—6 PSIG
Approximate Gas Velocity at Organic Reactant Injection Point—100 Ft./Sec.
Approximate Gas Velocity at Venturi Throat—500 Ft./Sec.
Quench Temperature—95° F.
Ratio of Recycle Quench to Reactants—40 to 1
Gas Velocity in Agglomerating Section—130 Ft./Sec.

After leaving the recycle loop, the material was neutralized with ammonia and the final product (essentially ammonium ether sulfate) had an analysis reflecting the following:
Active Content—61 wt.%
Unreacted Content (Carbon Tetrachloride Extract Procedure)—1.4 wt.% (As Is Basis)
Klett Color (5% Solution 40 mm. path)—45

EXAMPLE III

Alpha Olefin Sulfonate $C_{14}C_{16}$ Alpha Olefins (the organic reactant) were sulfonated under the following conditions in a reactor having a 1" venturi throat.
Organic Reactant Flow Rate—360#/hr.
$SO_3$ Flow Rate—158#/hr.
$SO_3$/Organic Reactant Mol Ratio—1.13/1
$SO_3$ Concentration—4.8 vol. %
Air Flow Rate—250 SCFM
Venturi Diameter at Throat—1"
Reaction Path Length—8"
Pressure at Upstream End of Venturi—13 PSIG
Pressure at Venturi Throat—6 PSIG
Approximate Gas Velocity at Upstream End of Venturi—100 Ft./Sec.
Approximate Gas Velocity at Venturi Throat—550 Ft./Sec.
Quench Temperature—90° F.
Ratio of Recycle Quench to Reactants—60 to 1
Gas Velocity in Agglomerating Section—130 Ft./Sec.

The product leaving the recycle loop was pumped through a digestion pipe for an additional 20 minutes hold-time, then neutralized with sodium hydroxide and hydrolyzed for 20 minutes at 300° F. The resulting product had an analysis reflecting the following:
Sodium Alpha Olefin Sulfonate—42.0 wt.%
Sodium Sulfate—0.9 wt.%
Unreacted Oil (Petroleum Ether Extract Procedure)—1.1 wt.% (As Is Basis)
Klett Color (unbleached) (5% Solution 40 mm. path)—380 Klett

EXAMPLE IV

A 50/50 mixture of high molecular weight (330) synthetic alkyl benzene and mineral oil with an approximate molecular weight of 350 was sulfonated under the following conditions in a reactor having a ¼" venturi throat:
Organic Reactant Flow Rate—34#/hr.
$SO_3$ Flow Rate—8#/hr.
$SO_3$/Organic Reactant Mol Ratio—1.02/1
$SO_3$ Concentration—5 vol. %
Air Flow Rate—12 SCFM
Venturi Diameter at Throat—0.25"
Reaction Path Length—2"
Pressure at Upstream End of Venturi—10 PSIG
Pressure at Venturi Throat—4 PSIG
Approximate Gas Velocity at Organic Reactant Injection Point—250 Ft./Sec.
Approximate Gas Velocity at Venturi Throat—510 Ft.Sec.
Quench Temperature—100° F.
Ratio of Recycle Quench to Reactants—20 to 1
Gas Velocity in Agglomerating Section—150 Ft./Sec.

The resulting product had an analysis reflecting the following:
Oil Soluble Sulfonic Acid—55 wt.%
Oil Insoluble Sludge—8 wt.%

The product was suitable as a base material for lube oil additives, or as a base for the chemical system used to enhance oil field recovery (i.e., in tertiary recovery systems).

EXAMPLE V

An aromatic mineral oil with approximately 30% sulfonatable content (as well as paraffins and other unreactive compounds) and molecular weight of 300 was sulfonated under the following conditions in a reactor having a ¼" venturi throat:

Organic Reactant Flow Rate—54#/hr.
SO$_3$ Flow Rate—5.2#hr.
SO$_3$ Concentration—4.0 vol. %
Air Flow Rate—10 SCFM
Venturi Diameter at Throat—¼"
Distance from Point of First Contact of Reactants to Downstream End of Venturi—2"
Pressure at Upstream End of Venturi—10 PSIG
Pressure at Venturi Throat—4 PSIG
Gas Velocity at Organic Reactant Injection Point—200 Ft./Sec.
Gas Velocity at Venturi Throat—480 Ft./Sec.
Organic Reactant Feed Temperature before Reaction—150° F.
Reaction Mixture Temperature from Reactor—180°–200° F.

The reaction mixture leaving the nozzle was not quenched, but was conveyed directly to the cyclone separator, because of its high melting point, and because color is not important. The liquid withdrawn from the cyclone separator was pumped to a sludge separator to remove the oil insoluble portion which settled as a bottom layer. Approximately 75% of the reaction mixture was recovered as the upper layer with an active content of 10% in the form of an aromatic, oil soluble sulfonic acid.

The foregoing detailed description has been given for clearness of understanding only and no unnecessary limitations should be understood therefrom as modifications will be obvious to those skilled in the art.

We claim:

1. A continuous process for reacting a gaseous sulfonating agent comprising sulfur trixoide with a sulfonatable liquid organic reactant to produce a reaction product, said process comprising the steps of:
   introducing said liquid organic reactant into a stream of said gaseous sulfonating agent;
   flowing said stream of gaseous sulfonating agent downwardly along a straight path from a point upstream of the location where said organic reactant is introduced;
   coaxially injecting said organic reactant downwardly into said gaseous stream from a location along said straight path;
   atomizing said liquid organic reactant to form a mist of organic reactant particles;
   at least partially atomizing said organic reactant before said introduction thereof into said stream of gaseous sulfonating agent;
   reacting said mist of organic reactant particles and said gaseous sulfonating agent in a temperature-increasing exothermic reaction to form a reaction mixture comprising particles of said reaction product;
   and then cooling said reaction product.

* * * * *

UNITED STATES PATENT AND TRADEMARK OFFICE
CERTIFICATE OF CORRECTION

PATENT NO. : 4,267,119
DATED : May 12, 1981
INVENTOR(S) : Burton Brooks and Richard Brooks It is certified that error appears in the above-identified patent and that said Letters Patent are hereby corrected as shown below:

Col. 3, line 19, "in Brooks" should be --in said Brooks--.

Col. 3, line 56, "struture" should be --structure--.

Col. 4, line 14, "communication" should be --communicates--.

Col. 5, line 1, "1/32' " should be --1/32"--.

Col. 7, line 7, "gas velocity is the" should be --gas velocity in the--.

Col. 12, line 57, "Ft.Sec." should be --Ft./Sec.--.

Col. 13, lines 22-23, "18-0" should be --180°--.

Signed and Sealed this

Twenty-eighth Day of July 1981

[SEAL]

Attest:

GERALD J. MOSSINGHOFF

Attesting Officer      Commissioner of Patents and Trademarks